US007262290B2

(12) United States Patent
Berrettini

(10) Patent No.: US 7,262,290 B2
(45) Date of Patent: Aug. 28, 2007

(54) DIAGNOSTIC MARKERS FOR MULTIPLE EPILEPSY PHENOTYPES

(75) Inventor: Wade H. Berrettini, Haverford, PA (US)

(73) Assignee: Trustees of the University of Pennsylvania, Philadelphia, PA (US)

(*) Notice: Subject to any disclaimer, the term of this patent is extended or adjusted under 35 U.S.C. 154(b) by 396 days.

(21) Appl. No.: 10/344,890

(22) PCT Filed: Aug. 24, 2001

(86) PCT No.: PCT/US01/26609

§ 371 (c)(1),
(2), (4) Date: Jul. 11, 2003

(87) PCT Pub. No.: WO02/18650

PCT Pub. Date: Mar. 7, 2002

(65) Prior Publication Data
US 2004/0014075 A1    Jan. 22, 2004

Related U.S. Application Data

(60) Provisional application No. 60/228,538, filed on Aug. 28, 2000.

(51) Int. Cl.
*C07H 21/04* (2006.01)
*C07K 14/00* (2006.01)
*C12Q 1/68* (2006.01)

(52) U.S. Cl. .................. 536/23.5; 435/6; 530/350
(58) Field of Classification Search .................. None
See application file for complete search history.

(56) References Cited

U.S. PATENT DOCUMENTS

| 5,210,016 A | 5/1993 | Blum et al. ............ 435/6 |
| 5,500,343 A | 3/1996 | Blum et al. ............ 435/6 |
| 6,500,938 B1* | 12/2002 | Au-Young et al. ......... 536/23.1 |

OTHER PUBLICATIONS

Takumi, T. et al. (1995) A novel ATP-dependent inward rectifier potassium channel expressed predominantly in glial cells. Journal of Biological Chemistry. vol. 270, pp. 16339-16346.*
Schoots et al. (1999) Co-expression of human Kir3 subunits can yield channels with different functional properties. Cell. Signal. vol. 11: 871-883.*
GenBank Accession No. U52155 (submitted Mar. 1996), 2 pages.*
Shuck et al. (1997) Cloning and characterization of two K+ inward rectifier (Kir) 1.1 potassium channel homologs from human kidney (Kir 1.2 and Kir 1.3). Journal of Biological Chemistry. vol. 272: 586-593.*
GenBank Accession No. U73192. (submitted Sep. 1996), 2 pages.*
Ferraro et al. (1999) Mapping loci for pentylenetetrazol-induced seizure susceptibility in mice. The Journal of Neuroscience. vol. 19: 6733-6739.*
Tada et al. (1997) Assignment of the glial inwardly rectifying potassium channel KAB-2/Kir4.1 (Kcnj10) gene to the distal region of mouse chromosome 1. Genomics. vol. 45: 629-630.*
Wacholder et al. Assessing the probability that a positive report is false: an approach for molecular epidemiolgy studies. Journal of the National Cancer Institute (2004) 96(6): 434-442.*
Tan et al. Genetic Association studies in Epilepsy: "The truth is out there". Epilepsia (2004) 45(11): 1429-1442.*
Buono et al. Association between variation in the human KCNJ10 potassium ion channel gene and seizure susceptibility. Epilepsy Research (2004) 58: 175-183.*
Doupnik et al. The inward recifier potassium channel family. Current Opinion in Neurobiology (1995) 5: 268-277.*
Ferraro et al. Quantitative genetic study of maximal electroshock seizure threshold in mice: evidence for a major seizure susceptibility locus on distal chromosome 1. Genomics (2001) 75(1-3): 35-42.*
Lenzen et al. Supportive evidence for an allelic association of the human KCNJ10 potassium channel gene with idiopathic generalized epilepsy. Epilepsy Research (2005) 63: 113-118.*
Shang et al. Functional characterization of missense variations in the Kir4.1 potassium channel (KCNJ10) associated with seizure susceptibility. Molecular Brain Research (2005) 139: 178-183.*
Lucentini et al. Gene Association Studies Typically Wrong. The Scientist (2004) vol. 18, 6 printed pages.*
Ioannidis et al. Replication validity of genetic association studies. Nature genetics (2001) 29:306-309.*

* cited by examiner

*Primary Examiner*—Jeffrey Fredman
*Assistant Examiner*—Angela Bertagna
(74) *Attorney, Agent, or Firm*—Licata & Tyrrell P.C.

(57) ABSTRACT

A mammalian KIR 4.1 gene and gene products which are predictive of a susceptibility or predisposition to neurological disorders such as multiple epilepsy phenotypes are provided. Methods of predicting an individual's susceptibility in developing or having a neurological disorder via detection of these diagnostic markers are also provided. In addition, compositions and methods for identifying compositions for use in the treatment of neurological disorders via these genes and gene products are described.

1 Claim, No Drawings

SEQUENCE LISTING

<160> NUMBER OF SEQ ID NOS: 2

<210> SEQ ID NO 1
<211> LENGTH: 2211

<212> TYPE: DNA
<213> ORGANISM: Homo sapiens

<400> SEQUENCE: 1

| | | | | | |
|---|---|---|---|---|---|
| ggcgctgcgg | agggagggg | cggcccggcc | cggcccagct | ctgccccgg | ccggcccgac | 60 |
| cccggccccg | gccccggac | aagcccttat | ctgatcccag | ctccgggttt | aagagtcctg | 120 |
| gcccggcccg | tcgcacagct | ctgctcctaa | ctcctgcccg | cccgtccgt | ccatctgtcc | 180 |
| cgctgccccg | cggcccatcc | aagggccact | ccacctcgga | cccaagatga | cgtcagttgc | 240 |
| caaggtgtat | tacagtcaga | ccactcagac | agaaagccgg | ccctaatgg | gcccagggat | 300 |
| acgacggcgg | agagtcctga | caaaagatgg | tcgcagcaac | gtgagaatgg | agcacattgc | 360 |
| cgacaagcgc | ttcccctacc | tcaaggacct | gtggacaacc | ttcattgaca | tgcagtggcg | 420 |
| ctacaagctt | ctgctcttct | ctgcgacctt | tgcaggcaca | tggttcctct | ttggcgtggt | 480 |
| gtggtatctg | gtagctgtgg | cacatgggga | cctgctggag | ctggaccccc | cggccaacca | 540 |
| cacccctgt | gtggtacagg | tgcacacact | cactggagcc | ttcctcttct | cccttgaatc | 600 |
| ccaaaccacc | attggctatg | cttccgcta | catcagtgag | gaatgtccac | tggccattgt | 660 |
| gcttcttatt | gcccagctgg | tgctcaccac | catcctggaa | atcttcatca | caggtacctt | 720 |
| ccaggcgaag | attgcccggc | caagaagcg | ggctgagacc | attcgtttca | gccagcatgc | 780 |
| agttgtggcc | tcccacaatg | gcaagccctg | cctcatgatc | cgagttgcca | atatgcgcaa | 840 |
| aagcctcctc | attggctgcc | aggtgacagg | aaaactgctt | cagaccccacc | aaaccaagga | 900 |
| aggggagaac | atccggctca | accaggtcaa | tgtgactttc | caagtagaca | cagcctctga | 960 |
| cagccccttc | cttattctac | cccttacctt | ctatcatgtg | gtagatgaga | ccagtccctt | 1020 |
| gaaagatctc | cctctttgca | gtggtgaggg | tgactttgag | ctggtgctga | tcctaagtgg | 1080 |
| gacagtggag | tccaccagtg | ccacctgtca | ggtgcgcact | tcctacctgc | agaggagat | 1140 |
| cctttgggc | tacgagttca | cacctgccat | ctcactgtca | gccagtggta | aatacatagc | 1200 |
| tgactttagc | cttttttgacc | aagttgtgaa | agtggcctct | cctagtggcc | tccgtgacag | 1260 |
| cactgtacgc | tacggagacc | ctgaaaagct | caagttggag | gagtcattaa | gggagcaagc | 1320 |
| tgagaaggag | ggcagtgccc | ttagtgtgcg | catcagcaat | gtctgatgac | ctgttcccac | 1380 |
| tccccatte | ctctggtctc | ttttcctctc | ttccaatgcc | ctggtaagga | atactacccg | 1440 |
| ggttactgg | agatccccg | aagcacccat | cctccactcc | ctcttcttta | acccagtggc | 1500 |
| ctgttggtag | cttaggccaa | ctggagtcca | ggttcgcctc | ccactgtccc | ctttccactt | 1560 |
| ccccagcttc | tgccccaata | cacatacctc | ccttaagcca | ggatggggga | aagagtggga | 1620 |
| ttaggctgaa | gtggcttaga | aggcctcagc | catgcttgga | tactcacatt | aggaggacca | 1680 |
| tgtggttgga | aggatagact | gccccctacc | tcccaccacc | accatgaagt | ttggtgactt | 1740 |
| gaggctggag | ctccctctgt | tacctttcca | tctgacggat | tccaaaggc | aagactctct | 1800 |
| ctgatggtca | cttttgtggtc | tgtgctttca | gaaatacagg | aatctgatat | caacatatcc | 1860 |
| tagggtttct | accaatctct | gttgaaagaa | gccagggttt | gccactgtga | agcttgattt | 1920 |
| ctgctggtga | cttctgacca | taagctagaa | ccatggtcgc | cactgttttc | cctctgtagt | 1980 |
| ttctcaagtg | aacactctca | ggatacccag | ttccctcata | gcctctgttc | tcagagaatt | 2040 |
| ggagttggcc | caagaaacat | aaacatataa | ccacccatat | ctatcctgga | ttctgaactc | 2100 |
| ttcaatttgg | agtgactaac | acaagttgtt | atctaaacct | ttaaacctat | cttccaggca | 2160 |
| gcccagagaa | gatctgtttc | cctgtgtcct | gtgaatggaa | ggacccgagc | c | 2211 |

<210> SEQ ID NO 2
<211> LENGTH: 379
<212> TYPE: PRT
<213> ORGANISM: Homo sapiens

<400> SEQUENCE: 2

```
Met Thr Ser Val Ala Lys Val Tyr Tyr Ser Gln Thr Thr Gln Thr Glu
  1               5                  10                  15

Ser Arg Pro Leu Met Gly Pro Gly Ile Arg Arg Arg Val Leu Thr
             20                  25                  30

Lys Asp Gly Arg Ser Asn Val Arg Met Glu His Ile Ala Asp Lys Arg
             35                  40                  45

Phe Pro Tyr Leu Lys Asp Leu Trp Thr Thr Phe Ile Asp Met Gln Trp
             50                  55                  60

Arg Tyr Lys Leu Leu Leu Phe Ser Ala Thr Phe Ala Gly Thr Trp Phe
 65                  70                  75                  80

Leu Phe Gly Val Val Trp Tyr Leu Val Ala Val Ala His Gly Asp Leu
                 85                  90                  95

Leu Glu Leu Asp Pro Pro Ala Asn His Thr Pro Cys Val Val Gln Val
                100                 105                 110

His Thr Leu Thr Gly Ala Phe Leu Phe Ser Leu Glu Ser Gln Thr Thr
                115                 120                 125

Ile Gly Tyr Gly Phe Arg Tyr Ile Ser Glu Glu Cys Pro Leu Ala Ile
            130                 135                 140

Val Leu Leu Ile Ala Gln Leu Val Leu Thr Thr Ile Leu Glu Ile Phe
145                 150                 155                 160

Ile Thr Gly Thr Phe Gln Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Cys Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335

Ala Ser Pro Ser Gly Leu Arg Asp Ser Thr Val Arg Tyr Gly Asp Pro
            340                 345                 350
```

```
Glu Lys Leu Lys Leu Glu Glu Ser Leu Arg Glu Gln Ala Glu Lys Glu
        355                 360                 365

Gly Ser Ala Leu Ser Val Arg Ile Ser Asn Val
    370                 375
```

DIAGNOSTIC MARKERS FOR MULTIPLE EPILEPSY PHENOTYPES

This application claims the benefit of priority of U.S. Provisional Patent Application Ser. No. 60/228,538, filed Aug. 28, 2000, which is herein incorporated by reference in its entirety.

This invention was supported in part by funds from the U.S. government (NIH Grant No. RO1 NS33243) and the U.S. government may therefore have certain rights in the invention.

FIELD OF THE INVENTION

The present invention relates to the identification of a mammalian gene, the human homolog of which is referred to as KIR 4.1, which is associated with the suscepetibility of an individual for developing or having a neurological disease or disorder such as multiple epilepsy phenotypes. The present invention encompasses nucleic acids, recombinant DNA molecules, and cloned genes and variants thereof of this susceptibility gene, gene products of this susceptibility gene, as well as cloning vectors containing the susceptibility gene molecules and host cells genetically engineered to express these molecules. The present invention also relates to methods of identifying compounds which modulate expression of this susceptibility gene and/or activity of proteins expressed thereby and to the use of these compositions as therapeutic agents in the treatment of these neurological diseases or disorders. In addition, the present invention relates to methods for diagnostic evaluation, genetic testing and prognosis of neurological diseases or disorders associated with this susceptibility gene. Identification of individuals with mutations in the sequences of the KIR 4.1 gene of the present invention is useful as a diagnostic aide for various neurological disorders and diseases, and in particular multiple epilepsy phenotypes.

BACKGROUND OF THE INVENTION

The term epilepsy refers to a complex series of over 40 diverse disorders that affect 1-2% of the population (Engle, J. Jr. Epilepsy Research 1996 26:141-150; McNamara J. Neurosci. 1994 14(6):3413-3425; Charlier et al. Nature Genetics 1998 18(1):53-56). The International League against Epilepsy periodically revises the classifications and publishes the nomenclature used to describe reported epilepsy phenotypes (Epilepsy, Intnl League Coalition 1989 30(4):389-399). The most common seizure phenotypes observed are idiopathic or primary generalized epilepsy (PGE), in which abnormal electrical activity spreads across the entire cerebral cortex, and focal epilepsy in which abnormal electrical activity is restricted to one brain region, usually the temporal lobe (TLE). Although recent studies have successfully identified specific genetic mutations in some rare seizure phenotypes, those genetic influences that predispose humans to common epilepsy types such as TLE and PGE are complex and poorly understood. Genetic influences on epilepsy have been the subject of several recent reviews (Ferraro, T. N. and Buono, R. J. "Genetics of Epilepsy: Mouse and Human Studies" In Genetic Influences on Neural and Behavioral Functions. eds. Plaff et al. 1999 CRC Press, Boca Raton, Fla.; Szepetowski, P. and Monaco, A. P. Neurogenetics 1998 1:153-163).

Family and twin studies have provided insights regarding the genetic influences on both PGE and TLE (Berkovic et al. Annals of Neurology 1998 43(4):435-45; Berkovic et al. Annals of Neurology 1996 40(2):227-235; Callenbach et al. Epilepsia 1998 39(3):331-6; Jain et al. Seizure 1998 7(2): 139-43; Miller et al. Genetic Epidemiology 1998 15(1):33-49). Concordance rates in monozygotic twins are reported to range between 65% and 95%, while concordance rates in dizygotic twins are reported at 15-30% (Stoffel, M. and Jan, L. Y. Nature Genetics 1998 18:6-8; Miller et al. Genetic Epidemiology 1998 15(1):33-49; Jain et al. Seizure 1998 7(2):139-43). Genetic influences in TLE phenotypes were documented more than 30 years ago and, more recently, in relatively benign idiopathic forms of TLE (Berkovic et al. Annals of Neurology 1996 40(2): 227-235; Neubauer et al. Neurology 1998 51(6):1608-12; Bray, P. F. and Wiser, W. C. Pediatrics 1965 36:207-211; Bray, P. F. and Wiser, W. C. N. Engl. J. Med. 1964 271: 926-933). These and other studies provide strong evidence for an inherited component to common forms of PGE and TLE. Since these disorders are not inherited in a simple Mendelian fashion, it appears that they arise from multiple gene mutations interacting with environmental factors. In addition, epidemiological evidence in humans demonstrates that relatives of probands with PGE or TLE are at increased risk for susceptibility to both generalized and focal epilepsy compared to individuals in the general population (Ottman et al. Archives of Neurology 1998 55:339-344), suggesting that different forms of epilepsy may share some susceptibility loci.

Linkage studies have lead to the identification of gene mutations that cause several rare epilepsy types and have suggested the chromosomal locations of genes related to a few more common epilepsy types. Juvenile myoclonic epilepsy (JME) has been the most studied of the PGE subtypes and evidence for linkage on chromosomes 6p and 15q have been reported (Greenberg et al. Amer. K. Medical Genetics 1988 31:185-192; Liu et al. Amer. J. Hum. Genet. 1995 57:368-381). In each case linkage data have been replicated in some independent patient groups (Weissbecker et al. Am. J. Human Genetics 1991 38:32-36; Elmslie et al. Human Molecular Genetics 1997 6(8):1329-1334), but not others (Whitehouse et al. Am. J. Hum. Genet. 1993 53:652-662; LeHellard et al. Epilepsia 1999 40(1):117-9; Sander et al., Am. J. Med. Genetics 1999 88(2):182-7), suggesting that several loci are involved in predisposition toward JME, most likely including loci on human 6p and 15q. Linkage on chromosome 8q has been reported for common subtypes of idiopathic generalized epilepsy such as childhood absence or juvenile absence, but not replicated in all patient groups tested (Zara et al. Human Molec. Genetics 1995 4(7):1201-1207; Durner et al. Am. J. Hum. Genet. 1999 64(5):1411-9; Fong et al. Am. J. Hum. Genet. 1998 63(4):1117-29; Sander et al. published the largest linkage study to date on a collection of European patients and family members with generalized epilepsy including JME, CAE, and Juvenile Absence Epilepsy (JAE) (Hum. Molec. Genet. 2000 9(10): 1465-1472). The results from this study provide evidence for a susceptibility locus on human chromosome 3q. This location was not previously reported in any other linkage study. Furthermore, the results did not replicate any evidence for linkage to 6P), 15q or 8q as previously reported by others (Greenberg et al. Amer. J. Med. Genet. 1988 31:85-92; Liu et al. Amer. J. Hum Genet. 1995 57:368-381; Weissbecker et al. Am. J. Hum. Genet. 1991 38:32-36; Elmslie et al. Hum. Molec. Genet. 1997 6(8):1329-1334). Thus the heterogeneity of the common epilepsy types continues to confound the search for seizure susceptibility factors.

Rare epilepsy types following Mendelian inheritance in families have lead to the identification of specific gene mutations that can cause seizure disorder in humans. Progressive myoclonic epilepsy (PME), a PGE subtype, shows linkage to markers on human chromosomes 6q and 21q (Serratosa et al. Hum. Molec. Genet. 1995 4(9):1657-1663; Sainz et al. Am. J. Hum. Genet. 1997 61(5):12-5-1209; Lehesjoki et al. Proc. Natl Acad. Sci. USA 1991 88(9):3696-9). PME of the Unverricht-Lundborg type was traced to a mutation in the gene encoding the protease cystatin B on 21q. PME of the Lafora type was traced to a mutation in the gene encoding a novel tyrosine phosphatase on 6q (Pennacchio et al. Science 1996 271:1731-4; Minassian et al. Nature Genetics 1998 20(2):171-4; Serratosa et al. Hum. Molec. Genet. 1999 8(2):345-52). Other PGE subtypes such as autosomal dominant nocturnal frontal lobe epilepsy (ADNFLE) and benign familial neonatal convulsions (BFNC) are linked to markers on human chromosomes 8q, and 20q (Lewis et al. Am. J. Hum. Genet. 1993 53:670-675; Wallace et al. J. Med. Genet. 1996 33(4):308-312; Leppert et al. Nature 1989 337:647-648; Phillips et al. Nature Genet. 1995 10(l):117-123). Mutations in two potassium ion channel genes (KCNQ2 and KCNQ3) have been identified as the BFNC loci on human chromosomes 8q and 20q (Biervert et al. Science 1908 279:403-406; Charlier et al. Nature Genetics 1998 18(1):53-56; Singh et al. Nature Genetics 1998 18(l):25-30); Stoffel, M. and Jan, L. Y. Nature Genetics 1998 18:6-8). In addition mutations in a nicotinic acetylcholine receptor alpha -4 subunit (CHRNA4) on 20q have teen linked to ADWFLE (Steinlein et al. Nature Genetics 1995 11(2):201-203: Steinlein et al. Hum. Molec. Genet. 1997 6(6):943-7) and mutations in a sodium ion channel SCN1B on 19q have recently been linked to generalized epilepsy with febrile seizures (GEFS, Wallace et al. Nature Genetics 1998 19:366-70). Partial epilepsy types are associated with regions on human chromosomes 2q, 10q and 15q (Scheffer et al. Annals of Neurology 1998 44(6):890-9; Ottman et al. Nature Genetics 1995 10:50-60; Poza et al. Annals of Neurology 1999 45(2):182-8; Neubauer et al. Neurology 1998 51(6):1608-12) and linkage on Xq and 8p has been detected in rare forms of epilepsy accompanied by mental retardation (Gendrot et al. Clinical Genetics 1994 45(3):145-153; Ryan et al. Nature Genetics 1997 17:92-95: Ranta et al. Genome Res. 1996 6(5):351-360). Finally there are additional reports of linkage on 19p for a familial form of febrile seizures (Johnson et al. Hum. Molec. Genet. 1998 7(1) :63-67) and 19q for benign familial infantile convulsions (Guipponi et al. Hum. Molec. Genet. 1997 6(3):473-477).

Although linkage studies have suggested the locations of genes for the common epilepsy forms such as JME, CAE, and TLE, these forms exhibit a high degree of clinical heterogeneity and the inheritance patterns are non-Mendelian, suggesting that multiple gene influences are responsible for most common seizure phenotypes. Alternative approaches are needed to help identify genes of partial effect in these common epilepsy types and to supplement the linkage work already accomplished and in progress.

One such alternative is to analyze epilepsy candidate genes for variations and then to demonstrate association of disease with inheritance of specific gene variants. This strategy has already been shown to be useful since a variation in a kainate type glutamate receptor is reported to be inherited in patients with idiopathic generalized epilepsy more often than predicted by classical genetics. (Sander et al. Am. J. Med. Genet. 1997 74:416-421)

Using a mouse model for epilepsy (Ferraro et al. Mammalian Genome 1997 8:200-208) , a susceptibility gene for seizures induced by various mechanisms was localized to a small region of murine chromosome 1 (Ferraro et al. J. Neuroscience 1999 19(16):6733-6739).

A sequence variation has now been identified in the homologous human gene, KIR 4.1. Further, it has now been determined that this variation occurs more frequently in epilepsy patients compared to matched controls.

SUMMARY OF THE INVENTION

The object of the present invention is to identify genes associated with neurological disorders, and in particular multiple epilepsy phenotypes, to provide methods of treating and diagnosing neurological disorders, and to provide methods for identifying compounds for use in these therapeutic and diagnostic methods.

In particular, an object of the present invention is to provide a mammalian gene comprising the human KIR 4.1 gene or a mammalian homologue thereof which is associated with neurological disorders or diseases, and in particular multiple epilepsy phenotypes, and molecules, cloned genes and variants thereof.

Another object of the present invention is to provide mammalian gene products encoded by the human KIR 4.1 gene or a mammalian homologue thereof, or fragments or variants thereof, and antibodies immunospecific for their gene products, or fragments or variants thereof.

Nucleic acid and amino acid sequences for the human KIR 4.1 gene are disclosed herein. Accordingly, another object of the present invention is to provide vectors, preferably expression vectors, comprising the nucleic acid sequence, and host cells genetically engineered to express mammalian susceptibility gene products.

Another object of the present invention is to provide methods of use of the human KIR 4.1 gene or mammalian homologues thereof, as well as gene products thereof, for the diagnostic evaluation, genetic testing and prognosis of a neurological disorder or disease, in particular an epilepsy phenotype. For example, in one embodiment, a method is provided for predicting the susceptibility or predisposition of an individual to having or developing a neurological disorder or disease such as an epilepsy phenotype by detecting for the presence or absence of the human KIR 4.1 gene or gene product or mutations thereof. In this method, the absence of the human KIR 4.1 gene or gene product or the presence of a mutation thereof is predictive of susceptibility or predisposition of an individual to having or developing a neurological disorder such as epilepsy. In another embodiment, a method is provided for diagnosing neurological disorders or diseases such as multiple epilepsy phenotypes in an individual by analyzing for the presence or absence of the human KIR 4.1 gene or gene product or a variant thereof in a biological sample obtained from the individual. In this method, the absence of the KIR 4.1 gene or gene product or the presence of a variant thereof is indicative of the individual having a neurological disease or disorder such as an epilepsy phenotype.

Another object of the present invention is to provide new treatments and methods of identifying new treatments for neurological disorders and disease such as multiple epilepsy phenotypes. In one embodiment, these treatments involve modulation of the expression of the human KIR 4.1 gene or a mammalian homologue thereof and/or the activity or synthesis of a gene product of the human KIR 4.1 gene or mammalian homologues thereof. In another embodiment, treatments involve supplying the mammal with a nucleic acid molecule encoding normal human KIR 4.1 or a mammalian homologue thereof. Methods for identifying new treatments involving modulation of the expression of the human KIR 4.1 gene or mammalian homologues thereof and/or the synthesis or activity of gene products of the human KIR 4.1 gene or mammalian homologues thereof comprise contacting a compound to a cell that expresses a human KIR 4.1 gene or a mammalian homologue thereof, measuring either the level of expression of a human KIR 4.1 gene or a mammalian homologue thereof or gene product activity produced by the cell and comparing this level to the level of expression or in the cell in the absence of the compound. Compounds which alter the level of expression and/or activity of human KIR 4.1 or mammalian homologues thereof are thus identified as modulators of this susceptibility gene.

DETAILED DESCRIPTION OF THE INVENTION

A sequence variation in human gene KIR 4.1 has now been identified as occurring more frequently in epilepsy patients compared to matched controls.

To identify polymorphisms in candidate genes in humans, DNA from patients with JME, CAE and mesial refractory TLE was analyzed. A combination of polymerase chain reaction (PCR), single strand conformational polymorphism (SSCP) and DNA sequencing was used for mutation detection from genomic DNA. Although only cDNA information is available for many candidate genes of interest, insertions, deletions and single nucleotide polymorphisms that may affect the coding portions of these genes can still be identified. For mutation detection, reverse transcription was utilized to generate cDNA pools that were used as a template and PCR was performed to generate amplified products for analyses by conformation sensitive gels and DNA sequencing.

Polymorphisms were first screened for in 30 unrelated TLE, 30 unrelated CAE and 30 unrelated JME patients. The number of patients who carry the variant out of the total screened yields a measure of "attributable risk". Not all persons who are ill from a complex disease would be expected to have increased risk for illness arising from a single genetic variation, thus attributable risk is a measure of mutation frequency in a given population.

Candidate selection based on mouse linkage data identified KIR 4.1 (also known as KCNJ10) as a high priority candidate gene for further testing. KIR 4.1 has a variation in its DNA coding region that alters an amino acid. In addition, a threonine residue at position 262 (found in the seizure resistant B6 strain of mice) is conserved in every other species from which KIR 4.1 has been sequenced including human, rat, and rabbit.

Thus, the human KIR 4.1 gene was searched for sequence variations. Like the mouse, the human gene contains no introns, a fact that greatly facilitated polymorphism detection. It was found that the human KIR 4.1 gene, like the mouse gene, has a missense mutation. The mutation in human KIR 4.1 is a single nucleotide polymorphism (T1037C of SEQ ID NO:1, C271R of SEQ ID NO:2) that alters the amino acid from a cysteine to an arginine in the putative dimerization domain of the ion channel subunit. Interestingly, this variation in the human gene (C271R) occurs in the same part of the protein as the mouse variation (a SNP causing T262S), just 9 amino acid residues apart from each other.

This single nucleotide polymorphism was analyzed by PCR and SSCP in 138 patients of German descent with idiopathic generalized epilepsy (IGE), juvenile absence epilepsy (JAE) and (CAE), 40 temporal lobe epilepsy (TLE) patients of European descent and 128 ethically matched controls. When all ill individuals were combined, chi square analysis of the distribution of genotpyes showed a significant difference between patients and controls ($\chi^2$:p<0.036). These data indicate that this polymorphism represents a protective allele against seizure susceptibility in multiple epilepsy phenotypes.

Accordingly, the human KIR 4.1 sequence and variants thereof serve as diagnostic markers for susceptibility to neurological disorders or diseases such as multiple epilepsy phenotypes.

The isolated nucleotide sequence of this susceptibility gene is depicted in SEQ ID NO:1. This mammalian gene is referred to herein KIR 4.1. This gene has also been referred to as KCNJ10. The deduced amino acid sequence of a gene product encoded by this nucleic acid sequence is depicted in SEQ ID NO:2. The absence of this mammalian gene or an encoded gene product or the presence of a variant gene or gene product thereof are believed to be indicative of the susceptibility of an individual to developing and/or having a neurological disorder or disease such as an epilepsy phenotype. An exemplary variant of the KIR 4.1 gene is the single nucleotide polymorphism T1037C of SEQ ID NO:1, C271R of SEQ ID NO:2 that alters the amino acid from a cysteine to an arginine in the putative dimerization domain of the ion channel subunit. Accordingly, the present invention relates to the KIR 4.1 gene and KIR 4.1 gene products and their use as diagnostic markers for ascertaining susceptibility or predisposition of an individual to developing and/or having a neurological disorder or disease such as an epilepsy phenotype. The KIR 4.1 gene and gene products and variants thereof are also useful in identifying new treatments and treating neurological disorders and diseases such as multiple epilepsy phenotypes.

As used herein by "KIR 4.1 gene" it is meant a nucleic acid molecule comprising the DNA sequence of SEQ ID NO:1; any DNA sequence that encodes a polypeptide containing the amino acid sequence comprising SEQ ID NO:2; and any DNA sequence that hybridizes to the complement of DNA sequences that encode an amino acid sequence comprising SEQ ID NO:2 under moderately stringent conditions. By "moderately stringent conditions" it is meant conditions such as those described by Ausubel et al. (1989 Current Protocols in Molecular Biology, Vol. I, Green Publishing Associates, Inc. and John Wiley & Sons, Inc. N.Y.). As used herein, "KIR 4.1 gene" also refers to degenerate variants encoding KIR 4.1 gene products. An exemplary variant of the KIR 4.1 gene is the SNP of T1037C of SEQ ID NO:1, C271R of SEQ ID NO:2 that alters the amino acid from a cysteine to an arginine in the putative dimerization domain of the ion channel subunit. KIR 4.1 genes can include both genomic DNA or cDNA and mRNA transcribed by the genomic DNA.

The present invention also relates to KIR 4.1 gene products. By "KIR 4.1 gene products" it is meant to include amino acid sequences encoded by the normal and variant KIR 4.1 genes. This term is also meant to include functionally equivalent KIR 4.1 gene products. By "functionally equivalent" it is meant a gene product with at least one biological activity which is the same as the normal KIR 4.1 gene product. Accordingly, contacting cells with a functionally equivalent KIR 4.1 gene product can inhibit or delay the onset of one or more symptoms of a neurological disorder or disease.

Also provided in the present invention are nucleic acid sequences, either DNA, RNA or a combination thereof which hybridize to the KIR 4.1 gene. Such hybridization may occur under moderately stringent conditions, or more preferably highly stringent conditions. Such conditions are well known in the art and discussed in detail in references such as Ausubel et al. (1989 Current Protocols in Molecular Biology, Vol. I, Green Publishing Associates, Inc. and John Wiley & Sons, Inc. N.Y.). These nucleic acid sequences can be used as probes in the detection of normal and variant KIR 4.1 genes. These nucleic acid sequences can also be used as antisense agents altering expression of normal or variant KIR 4.1 genes.

The present invention also relates to vectors comprising KIR 4.1 genes and nucleic acid sequences which hybridine to the KIR 4.1 gene. In a preferred embobiment, the vectors are expression vectors with a regulatory element which directs expression of the KIR 4.1 gene or the nucleic acid sequence. The present invention also relates to host cells genetically engineered to express KIR 4.1 gene products.

KIR 4.1 genes, KIR 4.1 gene products and variants thereof as well as nucleic acid sequences hybridizing to the KIR 4.1 gene are useful in diagnosing neurological disorders or diseases, identifying new treatments for neurological disorders or disease and in treating neurological disorders or disease. In a preferred embodiment, the neurological disorder or disease comprises one of the multiple epilepsy phenotypes.

In one embodiment, individuals with a predisposition to developing or having a neurological disorder such as an epilepsy phenotype are identified by detecting variations in the KIR 4.1 gene of SEQ ID NO:1 or an absence of the KIR 4.1 gene of SEQ ID NO:1. Methods for identifying individuals with a known nucleotide sequence or variants thereof are well known in the art. Examples of such methods include, but are not limited, polymerase chain reaction (PCR), ligase chain reaction (LCR) and nucleic acid sequence based amplification (NASABA). Reverse-transcriptase PCR (RT-PCR) is also a powerful technique which can be used to detect the presence of specific MRNA populations in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Hybridization to clones or oligonucleotides arrayed on a solid support (i.e. gridding) can also be used to detect the presence of a selected nucleotide sequence.

In this method a DNA-containing biological sample is obtained from an individual. DNA or mRNA in the biological sample is then analyzed for the presence or absence of the KIR 4.1 gene of SEQ ID NO:1 or a variant thereof. The absence of the KIR 4.1 gene of SEQ ID NO:1 and/or the presence of a variant gene is indicative of the individual being susceptible to developing or having a neurological disorder or disease such as an epilepsy phenotype. An exemplary variant KIR 4.1 is the SNP T1037C of SEQ ID NO:1.

Alternatively, biological samples obtained from an individual can also be analyzed for the presence of a variant KIR 4.1 gene product, such as those depicted in the presence or absence of the KIR 4.1 gene product of SEQ ID NO:2 to ascertain an individual's susceptibility to the neurological disorder. An exemplary variant gene product is the protein encoded by the SNP T1037C of SEQ ID NO:1, C271R of SEQ ID NO:2 that alters the amino acid from a cysteine to an arginine. Methods for detecting the presence or absence of a known polypeptide sequence are well known in the art. The KIR 4.1 gene product or variants and fragments thereof can be used to raise antibodies against the KIR 4.1 gene product or variant thereof. Such antibodies can then be used in various assays to detect the presence or absence of the KIR 4.1 gene product or variant thereof in a sample. Examples of these assays include, but are not limited to, radioimmunoassays, immunohistochemistry assays, competitive-binding assays, Western Blot analyses, ELISA assays, proteomic approaches, two-dimensional gel electrophoresis (2D electrophoresis) and non-gel based approaches such as mass spectrometry or protein interaction profiling. In these methods, the presence of a variant KIR 4.1 gene product or the absence of the KIR 4.1 gene product of SEQ ID NO:2 is indicative of an individual being susceptible to developing or having a neurological disorder or disease such as an epilepsy phenotype.

The KIR 4.1 gene and KIR 4.1 gene products of SEQ ID NO:1 and SEQ ID NO:2 also provide useful tools for development of new treatments for neurological disorders such as multiple epilepsy phenotype. For example, as demonstrated herein mutations in the nucleotide sequence of SEQ ID NO:1 leads to variants with disrupted protein function in individuals with an epilepsy phenotype. Accordingly, the KIR 4.1 gene product, agents which mimic the KIR 4.1 gene product or inhibit disruption in the function of the KIR 4.1 gene product may be useful in treating neurological disorders or disease such as multiple epilepsy phenotypes. Alternatively, agents which alter expression and/or levels of the normal protein may also be useful in the treatment of such disorders. Such agents can be identified in routine screening assays which examine levels of the KIR 4.1 gene or KIR 4.1 gene product as depicted in SEQ ID NO:1 and SEQ ID NO:2. Agents identified as altering levels and/or expression of the gene or gene product of SEQ ID NO:1 and SEQ ID NO:2 are expected to be useful in the treatment of neurological disorders such as multiple epilepsy phenotypes.

The KIR 4.1 gene and KIR 4.1 gene products of SEQ ID NO:1 and SEQ ID NO:2 are also useful in identifying other proteins and/or genes encoding such proteins which interact with KIR 4.1 gene products. Various methods for identifying such proteins and/or genes for encoding these proteins are known in the art. Well known techniques include, but are not limited to, yeast two hybrid systems and receptor binding assays.

What is claimed is:

1. A diagnostic marker for predicting susceptibility of an individual to having or developing idiopathic generalized epilepsy, juvenile absence epilepsy, childhood absence epilepsy, or temporal lobe epilepsy comprising an isolated human KIR 4.1 nucleic acid molecule of SEQ ID NO:1 or a human KIR 4.1 polypeptide of SEQ ID NO:2, wherein the thymine at position 1037 of the human KIR 4.1 nucleic acid molecule of SEQ ID NO:1 is replaced with cytosine, or the cysteine at position 271 of the human KIR 4.1 polypeptide of SEQ ID NO:2 is replaced with an arginine.

* * * * *